United States Patent
Shushunov

(12) 
(10) Patent No.: US 6,346,250 B2
(45) Date of Patent: Feb. 12, 2002

(54) COMPOSITION AND METHOD USEFUL FOR TREATING COLIC

(75) Inventor: Sergei Shushunov, Glencoe, IL (US)

(73) Assignee: LEV Laboratories Ltd., Glencoe, IL (US)

( * ) Notice: Subject to any disclaimer, the term of this patent is extended or adjusted under 35 U.S.C. 154(b) by 0 days.

(21) Appl. No.: 09/758,895

(22) Filed: Jan. 11, 2001

Related U.S. Application Data

(63) Continuation of application No. PCT/US00/06080, filed on Mar. 9, 2000.
(60) Provisional application No. 60/129,617, filed on Apr. 16, 1999.

(51) Int. Cl.[7] .................... A61K 39/385; A61K 47/00
(52) U.S. Cl. ................... 424/195.15; 514/783
(58) Field of Search ................ 514/783; 424/195.15

(56) References Cited

U.S. PATENT DOCUMENTS

| | | | | |
|---|---|---|---|---|
| 4,411,813 A | 10/1983 | Voisin | ......... | 252/312 |
| 4,902,850 A | 2/1990 | Davis | ......... | 585/817 |
| 5,480,646 A | 1/1996 | Vu | ......... | 424/443 |

FOREIGN PATENT DOCUMENTS

| | | |
|---|---|---|
| DE | 1255081 | 11/1967 |

OTHER PUBLICATIONS

Data base, Google.com., "RE:herbs for babies" starwatcher, May 1997.*
Data base, Google.com., Tri–light herbal remedies, Tummy Plus, 1997.*
Database, Druglaunch, "Mepaco herb colic", abstract, 1996.*
Database, Druglaunch, "babynos", abstract, 1996.*
"Fenicle tea or dimetricon medicine?", *Translated from: Norwegian Pharmaceutical Magasine No. 4/87*, Article Translated by Bjorn Egil Teig, BBA., 3 p.
"Stella Pharmaceutical Canada Inc. Company Information", *Drug Product Database*, http://www.hc–sc.gc.ca/hpb/drugs– dpd/compay/c5144.html., visited website on Jan. 31, 2000, 1 p.
Albert–Puleo, M., "Fennel and Anise as Estrogenic Agents", *Journal of Ethnopharmacology*, 2, pp. 337–344, (1980).
Brasil e Silva, G.A., et al., "Essential oil of foeniculum vulgare collected in Rio Grande do Sul", *Rev. Bras. Far., 54 (3)*, Database Caplus Abstract on STN, Acession No. 1976:21978, pp. 143–145, (1973).
Drinkwater, N.R., et al., "Hepatocarcinogenicity of Estragole (1–Allyl–4–methoxybenzene) and 1'–Hydroxyestragole in the Mouse and Mutagenicity of 1'–Acetoxyestragole in Bacteria", *J. Natl. Cancer Inst.*, 57 (6), pp. 1323–1331, (Dec. 1976).
Gervais, A., "Pediatric health: Colic", *Canadian Pharmaceutical Journal, 129 (7)*, Answer 1 of 1 EMBASE Copyright 2000 Elsevier Sci. B.V., pp. 27–28, (1996).
Mateson, I., "Fennel water or dimethicone in the treatment of colic in babies", *Nor. Farm. Tidsskr, 49 (4)*, Answer 1 of 1 Toxline, pp. 18–20, (1987).
Mohamed, Y.A., et al., "Spectrophotometric determination of certain volatile oils, Part III Assay of anethole in volatile oils of anise and fennel", *J. Pharm., 38 (5)*, Answer 24 of 34 CAPLUS Copyright 2000 ACS, pp. 117–199, (1976).
Weizman, Z., et al., "Efficacy of herbal tea preparation in infantile colic", *The Journal of Pediatrics*, pp. 650–652, (Apr. 1993).

* cited by examiner

*Primary Examiner*—William R. A. Jarvis
*Assistant Examiner*—Vickie Kim
(74) *Attorney, Agent, or Firm*—Mayer, Brown & Platt

(57) ABSTRACT

The invention provides compositions and methods that are useful for treating colic in mammals (e.g. human infants).

40 Claims, No Drawings

COMPOSITION AND METHOD USEFUL FOR TREATING COLIC

PRIORITY OF INVENTION

This application is a continuation of PCT Patent Application Serial No. PCT/US00/06080, filed on Mar. 9, 2000 which claims priority of invention under 35 U.S.C. §119(e) from U.S. provisional application No. 60/129,617, filed Apr. 16, 1999.

BACKGROUND OF THE INVENTION

Infantile colic is characterized by episodes during which an infant is irritable, cries or screams excessively, and draws up the legs. Episodes of colic tend to be worse in the evenings and do not respond to the usual means of comforting, such as feeding, cuddling, or diaper changing.

Infantile colic is common, occurring in approximately one in ten babies. It often first appears around the third or fourth week after birth, and usually clears up on its own by the age of twelve weeks. It is thought to be due to a spasm in the intestines, although there is no proof of this, and the cause of the presumed spasm is unknown. See The American Medical Association Encyclopedia of Medicine, Charles B. Clayton ed. 1989, Random House, New York, page 288.

In the past, colic has been treated with antispasmodic drugs, but these drugs are now not usually recommended for babies under 6 months of age. The most common treatment for colic today is to simply wait for the baby to grow out of the condition.

Z. Weizman et al. *The Journal of Pediatrics,* 1993, 122, 650–652 evaluated the effect of a beverage prepared from natural flavors, glucose, and dried extracts of 1) chamomile (*Matricaria chamomilla*), 2) vervain (*Verbena officinalis*), 3) licorice (*Glycyrrhiza glabra*), 4) fennell (*Foeniculum vulgare*) and balm-mint (*Melissa officinalis*) on infantile colic in a prospective double-blind study. It was found that the tea eliminated colic in 57% of the infants, whereas placebo was helpful in only 26% of the infants. Additionally, the mean colic score was reported to have been significantly improved in tea-treated infants.

Although some success in treating colic has been reported using herbal extracts, such preparations are not ideally suited for treating infantile colic. For example, it is difficult to accurately determine the dose of the active ingredient(s) in an extract or tea. It is also difficult to provide a reproducible dose using these materials. Finally, use of extracts and teas is limited due to the presence of contaminates that are present as a result of the manner in which the extracts and teas are prepared. The difficulties in determining an accurate dosage, and the presence of impurities are especially problematic for the treatment of infants, since infants can be significantly effected by small variations in dose or by the presence of small quantities of impurities.

Thus, there is currently a need for compositions and methods that are useful for treating colic. In particular, there is a need for methods and compositions that can conveniently be used for treating infants suffering from colic.

SUMMARY OF THE INVENTION

The present invention provides compositions that are useful for treating colic. Accordingly, the invention provides a composition comprising an aqueous emulsion of fennel oil.

The invention also provides a composition comprising 1) milk or formula and 2) fennel oil.

The invention also provides a therapeutic method for treating colic in a mammal comprising administering to a mammal in need of such therapy an effective amount of fennel oil.

The invention also provides a therapeutic method for treating colic in a mammal (e.g. a human) comprising administering to a mammal in need of such therapy an effective amount of a composition of the invention.

The invention also provides fennel oil having an estragole concentration of less than 2%.

The invention also provides a therapeutic method for treating colic in a mammal comprising administering to a mammal in need of such therapy an effective amount of anethole.

The invention also provides a composition comprising an aqueous emulsion of anethole.

The invention also provides a composition comprising 1) milk or formula and 2) anethole.

The invention also provides the use of 1) fennel oil, 2) water, milk, or formula, and optionally 3) an emulsifying agent to prepare a medicament useful for treating colic. Preferably, the medicament is in the form of an emulsion.

The invention also provides the use of 1) anethole, 2) water, milk, or formula, and optionally 3) an emulsifying agent to prepare a medicament useful for treating colic. Preferably, the medicament is in the form of an emulsion.

Representative compositions of the invention have been shown to be useful for treating colic (e.g reducing or eliminating one or more of the associated symptoms). The compositions provide a measurable, reproducible, and convenient source of fennel oil (or anrthole), that can readily be administered to infants. Thus, the compositions overcome difficulties associated with the use of extracts and teas.

DETAILED DESCRIPTION

Fennel oil is typically obtained from the dried ripe fruit of *Foeniculum vulgare* Miller (Fam Umbelliferae) by steam distillation. It comprises anethole [$C_{10}H_{12}O$] as the chief constituent (typically 50–90%, although amounts can vary depending on source), as well as d-pinene, phellandrene, dipentene, fenchone, methylchavicol, estragole, anisaldehyde and anisic acid. See Remmingtons Pharmaceutical Sciences, 18th ed. Alfonso R. Gennaro editor, 1990, Mack Publishing, Easton Pa. 1294; and PDR For Herbal Medicines, 1998, Medical Economics Company, Montvale N.J., 850–852. Fennel oil is commercially available from a variety of sources including Good Hope Botanicals, 830 Sweetser Ave., E, Novato, Calif., 94945, USA; and Polarome International, Inc., Jersey City, N.J., USA).

Estragole (1-allyl-4-methoxybenzene), is typically present in a concentration of 2–5% by weight in fennel oil from natural sources. Because estragole has been reported to produce mutagenic and carcinogenic effects in mice at certain doses (N. R. Drinkwater, *J. Natl. Cancer Inst.,* 1976, 57(6), 1323–133 1), the compositions of the invention preferably comprise fennel oil from a source that provides oil with a low concentration of estragole.

Additionally, applicant has discovered that compositions of the invention can be prepared from fennel oil wherein the concentration of estragole has been reduced. The concentration of estragole in fennel oil from a natural source can be reduced using any suitable separation technique known in the field of chemistry. For example, the concentration of estragole in fennel oil can conveniently be reduced by subjecting the oil to fractional distillation to remove estragole. Accordingly, fennel oil can be prepared having an estragole concentration of less than 2%, less than about 1%, less than about 0.5%, less than about 0.25%, less than about 0.2%, or less than about 0.1% weight percent.

The invention thus provides fennel oil having a reduced estragole concentration (e.g. a concentration of less than 2%, less than about 1%, less than about 0.5%, less than about 0.25%, less than about 0.2%, or less than about 0.1% by weight), which is useful for preparing the compositions of the invention.

Additionally, the concentration of anethole, an active ingredient in the compositions of the invention, can vary from 50–90% by weight in fennel oil from natural sources. As a result of this variability, it can be difficult to prepare compositions of the invention with a predictable anethole concentration using fennel oil from natural sources.

Applicant has discovered that the concentration of anethole in fennel oil can conveniently be standardized prior to preparing compositions of the invention. Anethole, in pure form, can be purchased commercially (for example, from Polarome, Inc., Jersey City, N.J., USA). Thus, fennel oil with a standardized concentration of anethole can be prepared by adding anethole to a natural oil (or an oil with a reduced estragole concentration) until a specific anethole concentration is obtained.

Thus, fennel oil having a standardized anethole concentration of at least about 55%, at least about 60%, at least about 65%, at least about 70%, or at least about 75% by weight can be prepared. For preparing the compositions of the invention, fennel oil having a standardized anethole concentration in the range of from about 55% to about 75% by weight (or preferably from about 60% to about 70%) can conveniently be used. Preferably, anethole is present in the fennel oil at a concentration of about 55±2%, about 60±2%, or about 65±2%.

As used herein, the term "fennel oil" includes fennel oil obtained from natural sources, as well as fennel oil having a reduced estragole concentration, fennel oil having a standardized anethole concentration, and fennel oil having both a reduced estragole concentration and a standardized anethole concentration.

The term "anethole" includes either stereoisomeric form of anethole (cis or trans), as well as mixtures thereof, it being well known in the art how to obtain a single isomeric form (for example, by separation, or by selective synthesis). Preferably, anethole is at least about 80%, 90%, 95%, 98%, or 99% trans.

The term "milk" includes human milk, cow's milk and goat's milk, and the like.

The term "formula" includes infant and baby formulae that are suitable for administration to mammals (e.g. humans or human infants). For example, the term includes commercially available milk based and soy based formulae, and the like, which are supplied in a form that is ready to use, or in a powdered form that can be mixed with a suitable liquid (e.g. water) prior to use.

The compositions of the invention can conveniently be in the form of an emulsion, i.e. a system containing two or more immiscible liquids in which one is dispersed in the form of very small globules throughout the other. Suitable emulsions can be prepared using techniques that are known in the art, for example, using techniques similar to those described in Remmingtons Pharmaceutical Sciences, 18th ed. Alfonso R. Gennaro editor, 1990, Mack Publishing, Easton Pa. 298–309, and 1519–1544. The invention also provides processes for preparing novel emulsions of the invention comprising mixing the components to provide the emulsion.

The compositions of the invention can conveniently comprise one or more pharmaceutically acceptable or food grade stabilizing agents, i.e., emulsifying agents. Suitable emulsifying agents or stabilizers are known in the art, for example, see Remmingtons Pharmaceutical Sciences, 18th ed. Alfonso R. Gennaro editor, 1990, Mack Publishing, Easton Pa., page 302. One emulsifying agent that can conveniently be used is polysorbate-80. The one or more stabilizing agents can be present in the compositions of the invention at any suitable concentration.

The specific and preferred values and embodiments listed below are for illustration only; they do not exclude other defined values, other values within defined ranges, or other embodiments disclosed herein.

Specifically, the invention also provides a composition for treating colic consisting essentially of fennel oil (or anethole) and water.

Specifically, the invention also provides a composition for treating colic consisting essentially of 1) milk or formula and 2) fennel oil (or anethole).

Specifically, the invention also provides a composition for treating colic consisting essentially of 1) fennel oil (or anethole), 2) water, and 3) one or more pharmaceutically acceptable stabilizers.

Specifically, the invention also provides a composition for treating colic consisting essentially of 1) milk or formula, 2) fennel oil (or anethole), and 3) one or more pharmaceutically acceptable stabilizers.

Specifically, the invention also provides a composition for treating colic consisting of fennel oil (or anethole) and water.

Specifically, the invention also provides a composition for treating colic consisting of fennel oil (or anethole), water, and one or more a pharmaceutically acceptable emulsifying agents.

Specifically, the invention also provides a composition for treating colic consisting of 1) milk or formula, and 2) fennel oil (or anethole).

Specifically, the invention also provides a composition for treating colic consisting of 1) milk or formula, 2) fennel oil (or anethole), and 3) one or more pharmaceutically acceptable stabilizers.

Specifically, the invention also provides a composition for treating colic comprising about 0.1 weight percent fennel oil (or anethole) and about 99.9 weight percent water.

Specifically, the invention also provides a composition for treating colic comprising about 0.1 weight percent fennel oil (or anethole), about 0.1 weight percent polysorbate-80 and about 99.8 weight percent water.

Specifically, the invention also provides a composition for treating colic comprising about 0.1 weight percent fennel oil (or anethole), about 0.1 weight percent polysorbate-80 and about 99.8 weight percent milk or formula.

Specifically, the invention also provides a composition for treating colic comprising about 0.05 to about 0.1 weight percent fennel oil, about 0.1 to about 0.5 weight percent emulsifying agent (e.g. polysorbate-80) and from about 99.85 to about 99.4 weight percent water.

Specifically, the invention also provides a composition for treating colic comprising about 0.05 to about 0.1 weight percent fennel oil, about 0.1 to about 0.5 weight percent emulsifying agent (e.g. polysorbate-80) and from about 99.85 to about 99.4 milk or formula.

Specifically, the composition of the invention can be in the form of an emulsion.

Specifically, in the compositions of the invention the fennel oil (or anethole) is preferably present in at least 0.05 weight percent.

Specifically, in the compositions of the invention the fennel oil (or anethole) is preferably present in at least 0.1 weight percent.

Specifically, in the compositions of the invention the fennel oil (or anethole) is present in a weight percentage of about 0.01 to about 1.0 percent.

Specifically, in the compositions of the invention the fennel oil (or anethole) is present in a weight percentage of about 0.05 to about 0.5 percent.

Specifically, in the compositions of the invention the fennel oil (or anethole) is present in a weight percentage of about 0.1 to about 0.2 percent.

Specifically, in the compositions of the invention the fennel oil (or anethole) is present in a weight percentage of about 0.1 percent.

Specifically, in the compositions of the invention, the fennel oil has a reduced estragole concentration of less than about 2%, and a standardized anethole concentration in the range of about 55% to about 75% by weight.

Specifically, in the compositions of the invention, the fennel oil has a reduced estragole concentration of less than about 1%, and a standardized anethole concentration in the range of about 60% to about 70% by weight.

Specifically, in the compositions of the invention, the fennel oil has a reduced estragole concentration of less than about 1%, and a standardized anethole concentration of about 55% to about 60% by weight.

Specifically, in the compositions of the invention, the fennel oil has a reduced estragole concentration of less than about 0.5%, and a standardized anethole concentration of about 55% to about 60% by weight.

Specifically, in carrying out the therapeutic methods of the invention, about 0.1 to about 20 mg/kg of fennel oil (or anethole) can be administered per day. More specifically, about 1 to about 15 mg/kg of fennel oil (or anethole) can be administered per day. Preferably about 5 to about 12 mg/kg of fennel oil (or anethole) can be administered per day.

Specifically, in the compositions of the invention, the ratio of stabalizing agents:fennel oil (or anethole) can be 1:1, 1:4, or 1:10, by weight or by volume.

Preferred compositions of the invention may exclude sodium bicarbonate or other related antacids.

Preferrably, the compositions and methods of the invention are useful for treating infantile colic in humans.

Specifically, the compositions of the invention described herein can be presented in the form of pharmaceutical compositions (or unit dosage forms) comprising an effective colic reducing amount of fennel oil and a pharmaceutically acceptable carrier. For example, the invention provides a pharmaceutical composition comprising an effective colic reducing amount of fennel oil (or anethole) and a pharmaceutically acceptable carrier.

The invention also provides a method for preparing a composition of the invention comprising, mixing fennel oil (or anethole) and water to provide an emulsion. Optionally, an emulsifying agent can be added. The method can conveniently be carried out using a high speed mixer or homogenizer.

For administration, the concentration of fennel oil in a liquid (e.g. aqueous) composition will generally be from about 0.01 to about 1.0 percent by weight. More specifically, the concentration of fennel oil can be about 0.25 to about 0.5 percent by weight, or from about 0.05 to about 0.2 percent by weight. Preferably, the concentration of fennel oil will be about 0.1 percent by weight.

When anethole is administered to treat colic according to a method of the invention, the concentration of anethole in a liquid (e.g. aqueous) composition will generally be from about 0.01 to about 1.0 percent by weight. More specifically, the concentration of anethole can be about 0.25 to about 0.5 percent by weight, or from about 0.05 to about 0.2 percent by weight. Preferably, the concentration of anethole will be about 0.1 percent by weight.

It may also be convenient to prepare concentrated solutions or emulsions, which can be diluted to an acceptable concentration (e.g. with water, milk or formula) prior to administration. Such concentrated solutions or emulsions may have the advantage of being easier to manufacture, store, or handle than solutions that are suitable for direct administration. Accordingly, the invention also provides compositions and emulsions containing fennel oil (or anethole) in concentrations that are multiples (e.g. 2, 5, 10, 20, 50, 75, or 90) of the concentrations that are conveniently administered.

The compositions of the invention can also contain a variety of inactive ingredients such as flavoring agents (e.g. cherry flavoring), sweetening agents (e.g. sucrose or fructose), preservatives, or dyes. Any material used in preparing a composition of the invention should be substantially non-toxic and suitable for consumption by the patient (e.g. a mammal).

The compositions of the invention have the advantage of providing a source of fennel oil (or anethole) that can conveniently be handled, shipped, stored, and administered. They also provide a source of fennel oil (or anethole) that can be administered in known and reproducible dosages, and that is free of unwanted contaminants. Thus, the compositions of the invention provide an advantage over teas and extracts. Additionally, the compositions of the invention have the advantage of providing fennel oil (or anethole) in a more concentrated form than is provided by a tea. For example, the concentration of fennel oil in a tea would typically be below about 0.01%.

A suitable dose of fennel oil (or anethole) can be in the range of from about 0.1 mg/kg per day to about 20 mg/kg per day. Specifically, a suitable dose can be in the range of about 1 mg/kg per day to about 15 mg/kg per day. More specifically, a suitable dose can be in the range of about 5 mg/kg per day to about 12 mg/kg per day. The desired dose can be presented in a single dose or as divided doses administered at appropriate intervals, for example, as two, three, four or more sub-doses per day. The sub-dose itself may be further divided, e.g., into a number of discrete loosely spaced administrations. The amount of a composition of the invention required for treatment will ultimately vary based on the severity of the condition and on the size and age of the patient. The required dose will ultimately be determined by the attendant physician or clinician, using techniques that are known in the art.

The ability of a composition of the invention to treat colic can be determined using pharmacological or clinical models which are well known to the art (see Z. Weizman et al. *The Journal of Pediatrics,* 1993, 122, 650–652), or using Test A described below.

Test A

A double blind, placebo controlled study was performed in order to evaluate the effects of a representative composition of the invention on colic. One hundred and twenty-one (121) infants under 12 weeks of age were randomized into treatment (n=62) and control (n=59) groups. Treatment group subjects received up to 1.5 ounces of an emulsion prepared from fennel oil (1 ml), polysorbate-80 (1 ml), and water (1000 ml). Control group subjects received placebo.

Colic was defined as a paroxysmal crying of 3 hours a day, at least 3 days a week, for 3 weeks (see Wessel MA *Pediatrics,* 1954, 14, 421–434). Only episodes of crying lasting more than 15 minutes were recorded. The outcome was measured as a decrease in cumulative weekly crying from baseline. Cure was considered when cumulative weekly crying dropped below 9 hours.

The treatment group had a cure rate of 65%, and the control group had a cure rate of 23.7%. Thus, the composition of the invention was found to be significantly more effective for treating colic than the placebo control.

The invention will now be illustrated by the following non limiting examples.

EXAMPLE 1

Preparation of a composition of the invention. One liter of fennel oil was combined in a mixing tank with one thousand liters of water, and the mixture was stirred at high speed with a homogenizer to provide an emulsion.

EXAMPLE 2

Preparation of a composition of the invention. One liter of fennel oil, one liter of polysorbate-80, and one thousand liters of water, were stirred together until an emulsion formed. The emulsion was found to be stable for an extended period of time (e.g. for months)

EXAMPLE 3

The following illustrate representative compositions of the invention, for therapeutic or prophylactic use in mammals (e.g. humans).

| (i) | Emulsion 1 (0.1 mg/ml) | mg/ml |
|---|---|---|
| | fennel oil | 0.1 mg |
| | water | q.s. ad 1 ml |
| (ii) | Solution 1 (emulsion) | Amount |
| | fennel oil | 0.1 ml |
| | stabilizing agent (e.g. polysorbate-80) | 0.1 ml |
| | water | 999.8 ml |
| (iii) | Solution 2 | |
| | fennel oil | 1.0 ml |
| | stabilizing agent (e.g. polysorbate-80) | 1.0 ml |
| | water | 998 ml |
| (iv) | Solution 3 (emulsion) | |
| | fennel oil | 1.0 ml |
| | stabilizing agent (e.g. polysorbate-80) | 4.0 ml |
| | water | 995 ml |
| (v) | Solution 4 | |
| | fennel oil | 10.0 ml |
| | stabilizing agent (e.g. polysorbate-80) | 40.0 ml |
| | water | 950 ml |
| (vi) | Concentrated Emulsion 1 | |
| | fennel oil | 25.0 ml |
| | stabilizing agent (e.g. polysorbate-80) | 25.0 ml |
| | water | 950 mL |
| (vii) | Concentrated Emulsion 2 | |
| | fennel oil | 25.0 ml |
| | stabilizing agent (e.g. polysorbate-80) | 100 ml |
| | water | 875 mL |

-continued

| (viii) | Concentrated Emulsion 3 | |
|---|---|---|
| | fennel oil | 500 ml |
| | stabilizing agent (e.g. polysorbate-80) | 500 ml |
| (ix) | Concentrated Emulsion 4 | |
| | fennel oil | 200 ml |
| | stabilizing agent (e.g. polysorbate-80) | 800 ml |

The above formulations may be obtained by conventional procedures well known in the pharmaceutical manufacturing art. Emulsions are prepared by mixing using techniques that are known in the art. "Fennel oil," as used in Example 3, can be fennel oil obtained from a natural source, fennel oil having a reduced estragole concentration, fennel oil having a standardized anethole concentration, or fennel oil having both a reduced estragole concentration and a standardized anethole concentration. In the above formulations (i–ix), anethole can be substituted for fennel oil to provide other representative compositions of the invention.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A therapeutic method for treating colic in a mammal comprising administering to a mammal in need of such therapy an effective amount of a composition comprising an aqueous emulsion of fennel oil, wherein the fennel oil has a reduced estragole concentration of less than about 1%, and a standardized anethole concentration in the range of about 55% to about 75% by weight.

2. The method of claim 1 wherein the composition consists essentially of 1) fennel oil; 2) water, and 3) one or more pharmaceutically acceptable emulsifying agents.

3. The method of claim 1, wherein the composition consists of 1) fennel oil; 2) water; and 3) one or more pharmaceutically acceptable emulsifying agents.

4. The method of claim 1, wherein the concentration of fennel oil in the composition is about 0.01 to 1.0 percent by weight.

5. The method of claim 1, wherein the composition further comprises one or more pharmaceutically acceptable or food grade emulsifying agents.

6. The method of claim 1, wherein the composition further comprises polysorbate-80.

7. The method of claim 6, wherein the ratio of polysorbate-80 to fennel oil is 1:1.

8. The method of claim 6, wherein the ratio of polysorbate-80 to fennel oil is 1:4.

9. The method of claim 6, wherein the ratio of polysorbate-80 to fennel oil is 1:10.

10. The method of claim 1, wherein the composition consists essentially of about 0.05 to about 0.1 weight percent fennel oil, about 0.1 to about 0.5 weight percent emulsifying agent and from about 99.85 to about 99.4 weight percent water.

11. The method of claim 1, wherein the composition consists of 0.5 to 0.1 weight percent fennel oil, 0.1 to 0.5 weight percent emulsifying agent and from 99.85 to 99.4 weight percent water.

12. The method of claim 1, wherein the fennel oil has a reduced estragole concentration of less than about 1%, and a standardized anethole concentration in the range of about 60% to about 70% by weight.

13. The method of claim 1, wherein about 0.1 to 20 mg/kg of fennel oil is administered per day.

14. The method of claim 1, wherein about 1 to 15 mg/kg of fennel oil is administered per day.

15. The method of claim 1, wherein about 5 to 12 mg/kg of fennel oil is administered per day.

16. The method of claim 1, wherein the concentration of fennel oil in the composition is about 0.01 to 1.0 percent by weight.

17. The method of claim 1, wherein the fennel oil has a standardized anethole concentration of 55±2%.

18. The method of claim 1, wherein the fennel oil has a standardized anethole concentration of 60±2%.

19. The method of claim 1, wherein the fennel oil has a standardized anethole concentration of 65±2%.

20. A therapeutic method of treating colic in a mammal comprising administering to a mammal in need of such therapy an effective amount of a composition comprising 1) milk or formula; and 2) fennel oil, wherein the fennel oil has a reduced estragole concentration of less than about 1%, and a standardized anethole concentration in the range of about 55% to about 75% by weight.

21. The method of claim 20, wherein the composition consists essentially of 1) milk or formula; 2) fennel oil; and 3) one or more pharmaceutically acceptable emulsifying agents.

22. The method of claim 20, wherein the composition consists of 1) milk or formula; 2) fennel oil; and 3) one or more pharmaceutically acceptable emulsifying agents.

23. The method of claim 20, wherein the concentration of fennel oil in the composition is about 0.01 to 1.0 percent by weight.

24. The method of claim 20, wherein the composition further comprises one or more pharmaceutically acceptable or food grade emulsifying agents.

25. The method of claim 20, wherein the composition further comprises polysorbate-80.

26. The method of claim 25, wherein the ratio of polysorbate-80 to fennel oil is 1:1.

27. The method of claim 25, wherein the ratio of polysorbate-80 to fennel oil is 1:4.

28. The method of claim 26, wherein the ratio of polysorbate-80 to fennel oil is 1:10.

29. The method of claim 20, wherein the composition consists essentially of about 0.05 to about 0.1 weight percent fennel oil, about 0.1 to about 0.5 weight percent emulsifying agent and from about 99.85 to about 99.4 weight percent milk or formula.

30. The method of claim 20, wherein the composition consists of about 0.05 to about 0.1 weight percent fennel oil, about 0.1 to about 0.5 weight percent emulsifying agent and from about 99.85 to about 99.4 weight percent milk or formula.

31. The method of claim 20, wherein the fennel oil has a reduced estragole concentration of less than about 1%, and a standardized anethole concentration in the range of about 60% to about 70% by weight.

32. The method of claim 20, wherein about 0.1 to 20 mg/kg of fennel oil is administered per day.

33. The method of claim 20, wherein about 1 to 15 mg/kg of fennel oil is administered per day.

34. The method of claim 20, wherein about 5 to 12 mg/kg of fennel oil is administered per day.

35. The method of claim 20, wherein the concentration of fennel oil in the composition is about 0.01 to 1.0 percent by weight.

36. The method of claim 20, wherein the fennel oil has a standardized anethole concentration of 55±2%.

37. The method of claim 20, wherein the fennel oil has a standardized anethole concentration of about 60±2%.

38. The method of claim 20, wherein the fennel oil has a standardized anethole concentration of 65±2%.

39. The method of claim 24, wherein the composition is an emulsion.

40. The method of claim 20, wherein the composition is an emulsion which comprises about 0.05 to about 0.1 weight percent fennel oil, about 0.1 to about 0.5 weight percent emulsifying agent and from about 99.85 to about 99.4 milk or formula.

* * * * *